United States Patent [19]

Bobst et al.

[11] Patent Number: 5,004,809

[45] Date of Patent: Apr. 2, 1991

[54] NITROXIDE LABELED NUCLEOTIDES AND NITROXIDE LABELED HYBRIDIZATION PROBES

[75] Inventors: Albert M. Bobst; Gary T. Pauley, both of Cincinnati, Ohio

[73] Assignee: University of Cincinnati, Cincinnati, Ohio

[21] Appl. No.: 826,064

[22] Filed: Feb. 4, 1986

[51] Int. Cl.$^5$ .............................................. C07H 17/00
[52] U.S. Cl. ........................................ 536/29; 536/22
[58] Field of Search ............................................ 536/29

[56] References Cited

FOREIGN PATENT DOCUMENTS 0070685  7/1982  European Pat. Off. .

OTHER PUBLICATIONS

Toppin et al., The Chemical Abstracts, 106:176793g (1987).
Pauly et al., The Chemical Abstracts, 107:231607x (1987).
Kao et al., Biochemistry 24, pp. 5465-5469 (1985).
Enzymatic Synthesis of Biotin–Labeled Polynucleotides: Novel Nucleic Acid Affinity Probes; Pennina R. Langer, Alex. A. Waldrop & David Ward; vol. 78, No. 11, pp. 6633-6637, Nov. 1981, Dept. of Human Genetics & Molecular Biophysics-Biochemistry, Yale University, New Haven, Connecticut.
Dipsticking the Major Groove of DNA with Enzymatically Incorporated Spin–Labeled Deoxyuridines by Electron Spin Resonance Spectroscopy; Albert M. Bobst, Shih-Chung Kao, Roland C. Toppin, John C. Ireland and Ingrid E. Thomas, reprinted from J. Mol. Biol. (1984), 173, 63-74, copyrighted 1984, Academic Press Inc. (London) Ltd.

*Primary Examiner*—Johnnie R. Brown
*Assistant Examiner*—James O. Wilson
*Attorney, Agent, or Firm*—Wood, Herron & Evans

[57] ABSTRACT

Nitroxide labeled hybridization probes are formed from novel nucleotides. The novel nucleotides are formed by substituting a nitroxide moiety at the C-5 position of the pyrimidine ring of either cytosine or uracil. The hybridization probes are formed by nick translation with *E. coli* polymerase I or T4 DNA polymerase or other template dependent enzymes. The hybridization probes can then be detected using electron spin resonance spectroscopy or alternately using a colorimetric method.

11 Claims, 1 Drawing Sheet

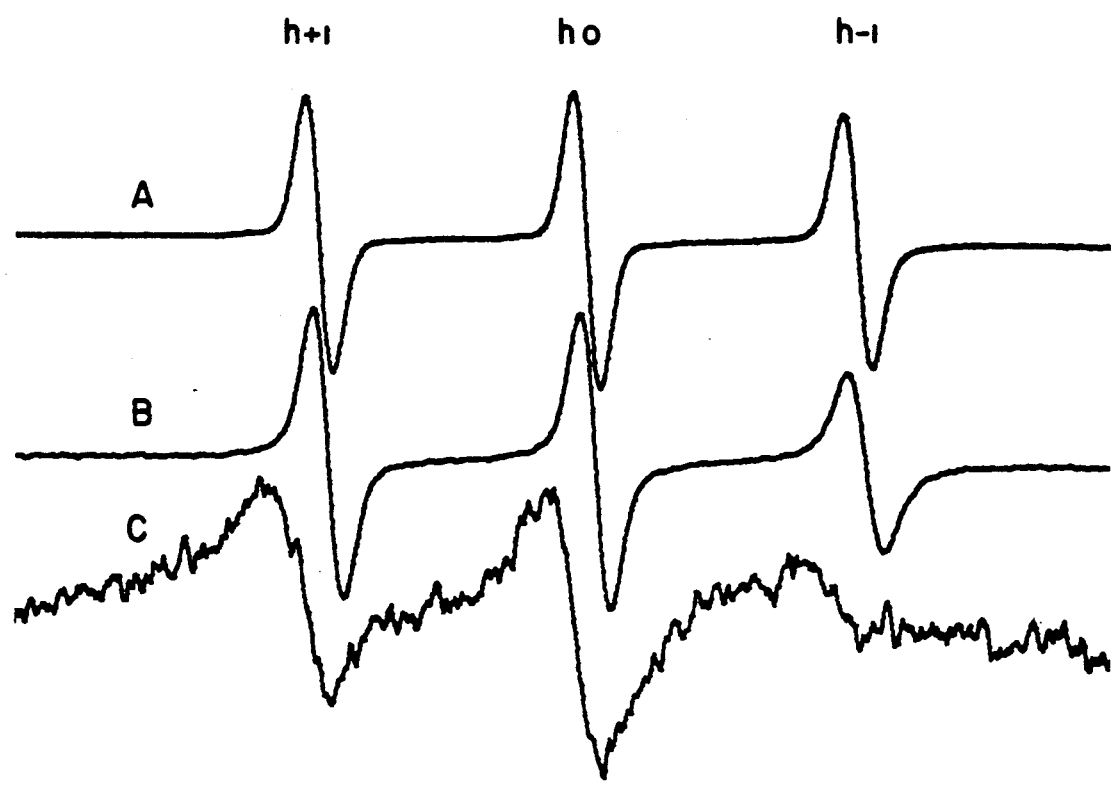

NITROXIDE LABELED NUCLEOTIDES AND NITROXIDE LABELED HYBRIDIZATION PROBES

BACKGROUND OF THE INVENTION

Many different techniques are currently used to identify nucleic acid sequences of deoxyribonucleic acids (DNA). Nick translation with *E. coli* polymerase I or polymerization with T4 DNA polymerase produces complementary DNA strands. By these approaches, hybridization probes, specific nucleic acid stretches which can be analytically identified, are formed. These hybridization probes can be used to identify some target DNA and RNA. This permits a scientist to detect the presence of specific DNA or RNA sequences in a genome.

There are different types of hybridization probes. By far the most commonly used hybridization probes contain radioactive DNA building blocks, wherein one of the atoms are radioactive and identifiable by radioactive assay methods. These radioactive DNA building blocks form excellent hybridization probes because they act in the same manner as a naturally occurring nucleic acid. In other words, the Pol I enzyme cannot distinguish the radioactive DNA building block from a non-radioactive one. The radioactively labeled nucleic acid stretches which contain the radioactive DNA building blocks are detected by X-ray film.

Radioactive hybridization probes present three distinct problems. The detection method for these probes involves multiple separation steps and cannot be conducted in solution preventing automation of genetic screening. More significantly, because of a much greater concern with the health and environmental hazards posed by these radioactive probes, appropriate safe handling of the hybridization probes is becoming more expensive and difficult. Finally, $^{32}P$ radiolabeled DNA probes are unstable and have a limited shelf life.

There are alternatives to radioactive hybridization probes. Probes which can be detected colorometrically are known. For example, Langer, in *Proceedings of the National Academy of Science*, Vol. 78, No. 11, pp. 6633–6637, Nov. 1981, discloses a biotin labeled nucleic acid. Specifically, Langer et al. report the production of a biotin labeled uridine triphosphate as well as a biotin labeled deoxyuridine triphosphate. Both of these building blocks are labeled with biotin at the C-5 position of the pyrimidine ring using an allylamine linker arm. The biotin labeled deoxyuridylic acid can be then incorporated into DNA using *E. coli* polymerase I. These hybridization probes are visualized by colorimetric assays.

There are problems with the colorimetric identification of biotin labeled DNA. Although kits have been made available by Enzo Biochem, Inc., New York or Bethesda Research Laboratories, Maryland, the required multiple steps for identification of biotin labeled DNA make it necessary to use specifically trained personnel. In addition, the color generating process that uses an enzyme to catalyze the synthesis of a colored or fluorescent molecule requires many hours for the visualization of the labeled DNA.

A number of nitroxide labeled nucleic acids have been reported, for example, Bobst et al in *Journal of Molecular Biology* (1984), 173, 63–74, reported various nitroxide labeled deoxyuridines wherein the nitroxide group was attached to the C-5 position of the pyrimidine ring. The structures reported are set forth below.

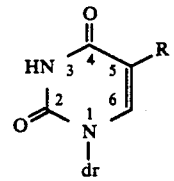

DUMMT

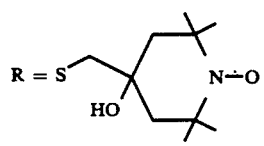

DUTT

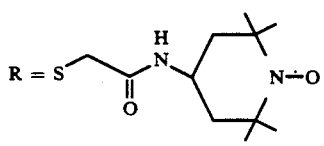

DUMPT

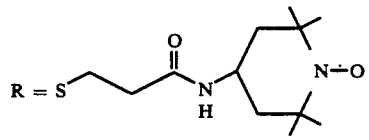

DUMBT

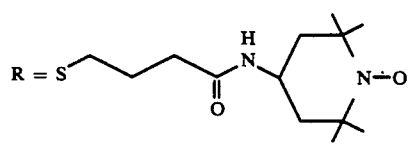

Further, these nitroxide labeled nucleic acids can be identified by electron spin resonance spectroscopy. Such a method is advantageous since it can be conducted using solution chemistry which greatly simplifies the identification process. Bobst et al also determined that these nitroxide labeled nucleic acids could be incorporated into nucleic acid homopolymers using terminal transferase. However, they were not taken up by the Pol I enzyme in nick translation experiments or by the T4 DNA polymerase with double stranded DNA as a template. Therefore these are totally unsuitable for use in formation of hybridization probes using template specific enzymes.

SUMMARY OF THE INVENTION

The present invention is premised upon the realization that a nitroxide labeled deoxyuridine or deoxycytidine will be incorporated into a DNA strand by Pol I or T4 DNA polymerase if the nitroxide moiety is attached to the C-5 position of the pyrimidine ring of the deoxyuridine or deoxycytidine via a tether, whereby the linkage between the C-5 position of the pyrimidine ring and the tether containing the nitroxide moiety is a C—C bond. The carbon (C) of the tether can either be a methylene (—CH$_2$—) or methenylene (—CH=). For some unknown reason, the C—C linkages do not interfere with the incorporation of the nitroxide labeled nucleic acid building block in nick translation by Pol I or in DNA polymerization with T4 DNA polymerase.

The nitroxide labeled hybridization probes are highly advantageous with respect to either the radioactive probes or the biotin labeled probes, which are detected colorimetrically, because the probes of the present invention can be identified very simply and relatively inexpensively. The nitroxide moiety can be identified using electron spin resonance over a relatively narrow wave band. Therefore, a dedicated electron spin resonance spectrometer can be used which is designed to scan only that narrow wave band. Further, since the nitroxide moiety displays three very distinct peaks, the dedicated electron spin resonance spectrophotometer can use a time averaging technique to identify relatively small quantities of the hybridization probe reliably. Such a dedicated spectrometer is less expensive than currently available spectrometers. Further, the electron spin detection of the nitroxide labeled moieties is extremely fast, simple and can be accomplished in solution. Accordingly, this permits extremely rapid detection of complementary nucleic acid sequences and the process can be readily automated.

These and other advantages of the present invention will be appreciated in light of the detailed description and drawing. in which:

BRIEF DESCRIPTION OF THE DRAWING:

The FIGURE shows three typical ESR spectra of nitroxide labeled nucleotides in different situations. (A) Nitroxide labeled nucleic acid building block, (B) Nitroxide labeled single stranded DNA, (C) Nitroxide labeled double stranded DNA. The example shown is specific for a DUAT containing system.

DETAILED DESCRIPTION

According to the present invention, nucleic acid triphosphates, which can be identified by electron spin resonance and which can be incorporated through nick translation into a DNA strand are formed from bases either uracil or cytosine which is substituted at the C-5 position of the pyrimidine ring with a carbon atom or tether and wherein the carbon atom or tether is further substituted with a nitroxide containing moiety. The nucleotide or acid triphosphate for use in the present invention has the following general formula:

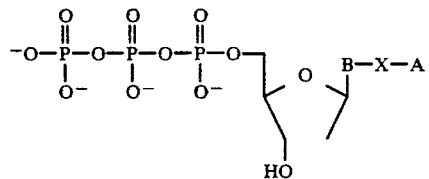

Formula 1

Wherein B represents either cytosine or uracil;

X represents the tether group and is selected from the groups consisting of methenylene (—CH=) and methylene (—CH$_2$—) and is bonded by a single bond t the C-5 position of the pyrimidine ring of B; and A represents the nitroxide containing moiety.

The negative charges are of course taken up or balanced by biologically acceptable counterions such as Na+ as is well known in the art.

Generally the nitroxide containing moiety will have the following general formula:

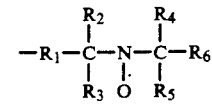

Formula 2

In this formula $R_1$ represents substituted or unsubstituted $C_1$-$C_{15}$ alkylene.

$R_2$ and $R_4$ represent $C_1$-$C_{15}$ alkyl or combined (i.e., wherein $R_2$ and $R_4$ are bonded to each other to form a cyclic compound) represents $C_2$-$C_{15}$ alkylene, $C_2$-$C_{15}$ alkylene ether (i.e., where an O is contained in the ring), $C_2$-$C_{15}$ alkylene amido, (i.e., where a N is contained in the ring);

$R_3$, $R_5$, $R_6$ represent $C_1$-$C_5$ alkyl.

In all of these formulas the terms alkylene and alkyl ar intended to include unsaturated and saturated moieties. Substituted refers to internal and external substitution of the alkylene group. Internal substitution for example refers to alkylene—amido—alkylene, alkylene—ester—alkylene, alkylene-ether-alkylene structures. External substitution refers to such structures as hydroxy alkylene or where an acid, ester or amide moiety are attached to the alkylene group in place of one hydrogen.

More preferably A will represent one of the five formulas shown in formulas 3a-e.

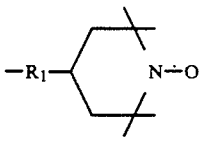

Formula 3a

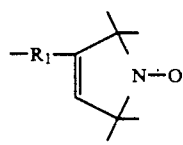

Formula 3b

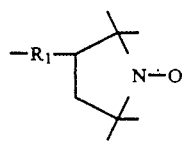

Formula 3c

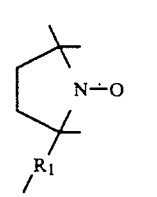

Formula 3d

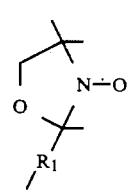

Formula 3e

These labeled nucleic acid triphosphates are formed by known procedures. According to one method the base, either cytosine or uracil, bound to the deoxyribose triphosphate, is reacted with allylamine to substitute the allylamine to a mercurated C-5 position of the pyrimidine ring. The nitroxide labeled moiety is then substituted onto the nitrogen of the allylamine to form a pyrimidine ring substituted at the C-5 position with an alkylidyne amido nitroxide moiety. This is similar to the method practiced by Langer et al to substitute biotin to the C-5 position of the pyrimidine ring to form a colorometrically detectable hybridization probe.

More specifically, the unlabeled nucleoside triphosphate, either the uracil or cytosine based nucleoside such as 2'-deoxyuridine-5'-triphosphate is dissolved in an aqueous buffer solution such as sodium acetate buffer solution at a pH of 6.0 or 7.0. This is mercurated by adding a mercury salt such as mercuric acetate. After a period of several hours the reaction product is cooled and a chloride is added such as lithium chloride. The reaction is then extracted with, for example, ethyl acetate and then the mercurated nucleoside triphosphate is precipitated from the aqueous layer by the addition of cold ethanol.

The mercurated nucleoside triphosphate is added without further purification into an aqueous sodium acetate buffer solution and a linker compound is added to the solution. Preferably the linker will be an allylamine. For purposes of biological activity the amine is not essential, however it is very important that a carbon atom substitutes the mercury on the mercurated nucleotide. The amine is there merely to facilitate the addition of the nitroxide group to the nucleotide. Other functional groups such as carboxyl or hydroxyl can also be used in similar reactions t facilitate this addition.

The allylamine is prepared by adding distilled allylamine to an ice cold 4M acetic acid solution. This is neutralized with concentrated sodium hydroxide. The solution is added together with a catalyst such as potassium tetrachloropalladate II. After short vortexing the solution is left standing for about 18 hours and is centrifuged to remove a black precipitate. The supernatant is passed over a column of Dowex (sodium form) before isolating the allylamine nucleotide by chromatography over DEAE-Sephadex with triethylammonium carbonate gradient.

The double bond of the allyl group of the allylamine nucleotide can be reduced by hydrogenation using 10% palladium on carbon as a catalyst in solution.

The nitroxide moiety is added to the linker compound, either allylamine or other linker compound, by first forming a nitroxide moiety which includes a complimentary reactive group such as a carboxylic acid group. The nitroxide compound such as 4-oxo-2, 2, 6, 6-tetramethyl-piperidinooxy can be purchased. A carboxylic acid group can then be added to the compound by various methods. For example, the above nitroxide molecule can be reacted with tosylmethyl isocyanide dissolved in dimethoxyethane. Subsequently potassium t-butoxide is dissolved in an equimolar solution of dimethoxyethane and t-butyl alcohol and added to the solution of nitroxide compound. After stirring for about an hour at 0° C., it is allowed to warm to room temperature and is subsequently quenched with water and extracted with ethyl ether. Upon evaporation of the ether, a solid product is obtained which is dissolved in methanol and added to a solution of barium hydroxide and sodium hydroxide and heated to reflux for about 24 hours. After cooling to room temperature, this is extracted with portions of chloroform which are discarded. The aqueous phase is acidified to a pH of about 2.0 with hydrochloric acid and extracted with chloroform, the chloroform is dried over magnesium sulfate and the carboxylated nitroxide compound remains.

The carboxylated nitroxide compound is then reacted with N-hydroxysuccinamide and N,N'-dicyclohexylcarbodiimide in an appropriate solvent such as N,N-dimethyl formamide. Subsequently the solution is centrifuged to remove the formed precipitate. The succinamide ester nitroxide compound remains in the supernatant and it is isolated by TLC with methanol/chloroform.

These are activated spin labels which can then be reacted with the modified nucleotides to form the spin labeled nucleoside triphosphates of the present invention. More specifically, the modified nucleotides are dissolved in a buffer solution, for example sodium borate buffer pH of 8.7. The activated spin label compound is then dissolved in an appropriate solvent such as N-N'-dimethylformamide and added to the modified nucleotide buffer solution. After about 4 hours of stirring at room temperature, the spin labeled nucleotide is formed.

The spin labeled nucleoside is purified by DEAE-Sephadex chromatography eluted with a gradient of 0.1–0.5M ammonium bicarbonate. Additional purification can be achieved by preparative paper chromatography using Whatman 3MM paper eluted with ethanol/1.0M sodium acetate or by HPLC with a micro-Bondapak C-18 column eluting with a step gradient (500 mM ammonium phosphate pH 7.5 (150 sec.) and 1:1 (v/v) ammonium phosphate pH 7.5/methanol-water (11:9, v/v) (999 sec.)).

Paper chromatography or HPLC purification is always followed by a final DEAE-sephadex chromatography step to remove the nonvolatile salts and by lyophilization.

The formation of these compounds will be further appreciated in light of the following examples:

EXAMPLE 1

Synthesis of Modified Nucleoside Triphosphate pppDUAA 58 mg (0.1 mmol) of 2'-deoxyuridine-5'-triphosphate are dissolved in 10 ml of 0.1M sodium acetate buffer pH 6.0. 160 mg (0.5 mmol) mercuric acetate are added and the reaction is stirred at 50° C. After 4 hours the reaction is cooled on ice and 43 mg (1.0 mmol) of lithium chloride are added. The reaction is extracted 5 times with an equal volume of ethyl acetate to remove excess $HgCl_2$. The nucleotide mercurated at the C-5 position of the pyrimidine ring is then precipitated from the aqueous layer by addition of 3 volumes of cold ethanol, collected by centrifugation, washed first with cold ethanol, then with ethyl ether, and finally air dried.

The mercurated nucleoside triphosphate is added without further purification to 5.0 ml of 0.1M sodium acetate buffer pH 5.0. A freshly made solution of allylamine is prepared by adding 0.5 ml of freshly distilled allylamine to 2.8 ml of ice cold 4M acetic acid, and the solution is then neutralized with concentrated sodium hydroxide. 0.6 ml of the allylamine stock, together with 65 mg (0.2 mmol) of potassium tetrachloropalladate II are added to the nucleoside solution. After short vortexing the solution is left standing for 18 hours before centrifuging it to remove the black precipitate. The supernatant is then passed over a column of Dowex (sodium form) before isolating the allylamine nucleoside triphosphate (pppDUAA) by chromatography over DEAE-Sephadex with a 0.2 to 1.0M triethylammonium carbonate gradient. The yield of this reaction is typically 0.03 to 0.04 mmoles. The structural formula of pppDUAA is as:

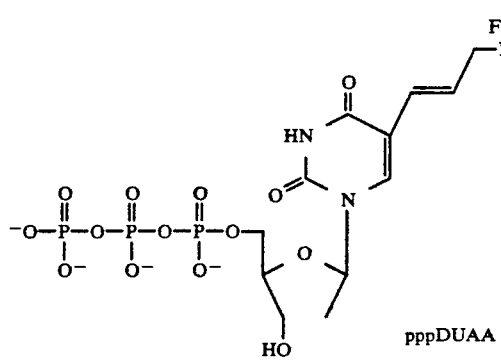

Formula 4
pppDUAA

EXAMPLE 2

Synthesis of Modified Nucleotide Triphosphate pppDCAA 50 mg (0.1 mmole) of 2'-deoxycytidine-5'-triphosphate are dissolved in 20 ml of 0.1M sodium acetate buffer at pH 7.0. 280 mg (0.9 mmol) mercuric acetate are added and the reaction is stirred at 50C. After 4 hours the reaction is cooled on ice and 84 mg (2.0 mmol) of lithium chloride are added. The reaction is extracted five times with an equal volume of ethyl acetate. The mercurated nucleotide triphosphate is then precipitated from the aqueous layer by the addition of three volumes of cold ethanol, collected by centrifugation, washed with cold ethanol, washed with ethyl ether, and air dried.

The mercurated nucleoside triphosphate is added without further purification to 6.0 ml of 0.1M sodium acetate buffer at pH 5.0. A fresh solution of allylamine is prepared by adding 0.5 ml of allylamine to 1.5 ml ice cold 4M acetic acid, before neutralizing the solution with concentrated sodium hydroxide. 0.35 ml of the freshly prepared allylamine stock, together with 70 mg (0.2 mmol) of potassium tetrachloropalladate II are added to the nucleotide solution. After brief vortexing, the reaction is left in the dark undisturbed. After 12 hours the solution is centrifuged to remove the black precipitate and passed over a column packed with celite. The allylamine nucleoside triphosphate (pppDCAA) is then isolated by chromatography over DEAE-Sephadex, eluted with a 0.2-1.0M gradient of triethylammonium carbonate. pppDCAA is finally passed over a Dowex column (sodium form). The yield of this reaction is typically 0.02 mmoles. pppDCAA has the following structural formula:

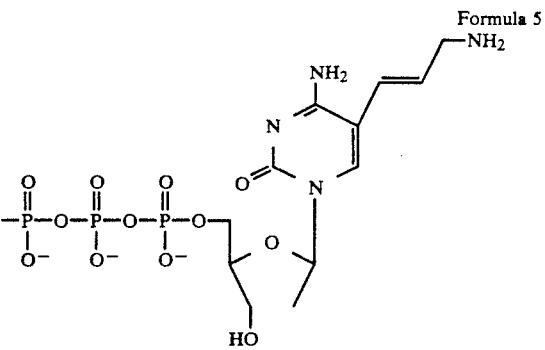

Formula 5

EXAMPLE 3

Synthesis of Modified Nucleoside Triphosphate pppDUPA pppDUAA (formula 4) 0.042 mmol is dissolved in 20 ml of water in a 100 ml round bottom flask. Palladium (20 mg-10% on carbon) is added and the solution is saturated with hydrogen. The solution is then stirred under a hydrogen filled baloon for 4 hours before filtering through Celite. The pppDUPA is isolated by DEAE-Sephadex chromatography with a 0.2 to 1.0M triethylammonium carbonate gradient. The conversion is essentially quantitative.

The formula of pppDUPA is:

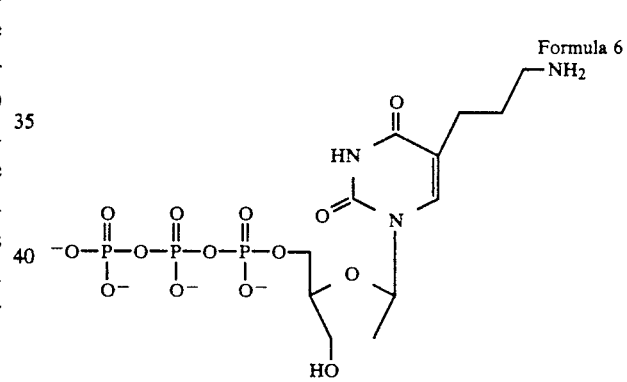

Formula 6

The synthesis of activated nitroxide compounds is further disclosed by the following examples:

EXAMPLE 4

Synthesis of Activated 6-member Ring Label 4-oxo-2,2,6,6-tetrametyl-piperidinooxy was converted to 4-carboxylic acid-2,2,6,6-tetranethyl-piperidinooxy by the method of Rauckman (1976). 5.0 g (300 mmol) of 4-OXO-2,2,6,6-tetramethyl-piperidinooxy together with 5.9 g (300 mmol) of tosyl-methyl isocyanide are dissolved in 175 ml of dimethoxyethane at 0° C. Then 6.8 g (600 mmol) of potassium t-butoxide dissolved in 80 ml of 1:1 dimethoxyethane:t-butyl alcohol at 0° C. are added. The solution is now stirred for 1 hour at 0° C. before allowing it to warm up to room temperature for an additional one hour of stirring. The reaction is then quenched with 700 ml of water and extracted 4 times with 250 ml portions of ethyl ether. Upon evaporation of the ether 3.71 g of red crystals are collected. These crystals are then dissolved in 60 ml of methanol and added to a solution of 12 g of barium hydroxide and 1.0 g of sodium hydroxide in 200 ml of water. This solution is heated to reflux 24 hours, cooled to room temperature, and extracted twice with 100 ml portions of chloroform which are discarded. The aqueous phase is acidified to pH 2.0 with 20% HCl and extracted 4 times with 100 ml portions of chloroform. The chloroform is dried over magnesium sulfate and gives 1.9 g of 4-carboxylic acid-2,2,6,6, tetramethyl-piperidinooxy upon evaporation.

500 mg (2.5 mmol) of 4-carboxylic acid-2,2,6,6, tetramethyl-piperidinooxy are stirred with 288 mg (2.5 mmol) of N-hydroxysuccinamide and 515 mg (2.5 mmol) of N,N'-dicyclohexylcarbodiimide in 20 ml of N,N-dimethyl formamide at 50° C. for 18 hours. Subsequently the solution is centrifuged to remove the precipitate. From the supernatant 705 mg of 7 are isolated by preparative TLC with methanol/chloroform (1:19, v/v). This activated 6-member ring label has the following general formula:

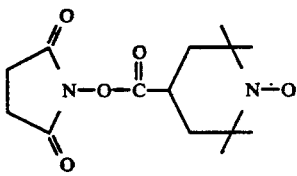

Formula 7

EXAMPLE 5

Synthesis of Activated 5-member Ring Label:

500 mg (2.72 mmol) of 2,2,5,5-tetramethyl-3-pyrrolin-1-oxyl-3-carboxylic acid are stirred with 313 mg (2.72 mmol) of N-hydroxysuccinamide and 560 mg (2.72 mmol) of N,N'-dicyclohexylcarbodiimide in 20 ml of N,N'-dimethyl formamide at 50° C. for 18 hours. The solution is then centrifuged to remove the precipitate and the supernatant gives 717 mg of the compound shown in Formula 8 after preparative TLC with methanol/chloroform (1:19, v/v). The activated 5-member ring label has the following general formula:

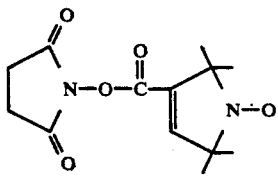

Formula 8

EXAMPLE 6

Synthesis of Activated 5-aminovaleric-amide-5-member Ring 117 mg (1.0 mmol) of 5-aminovaleric acid are dissolved in 5 ml of triethylamine saturated water which was adjusted to pH 10.0 by bubbling carbon dioxide into the solution. 388 mg (1.0 mmol) of the compound shown with formula 8 are dissolved in 4 ml of N,N'-dimethyl formamide and added slowly to the above solution and stirred for 18 hours at 50C. The solution is then evaporated to 1 ml and after preparative TL with methanol/chloroform/HCl (1:10:0.05) 300 mg of 9a as yellow oil, which is diluted with 3 ml of N,N'-dimethyl formamide. To this solution another 3 ml of N,N'-dimethyl formamide containing 117 mg (1.0 mmol) of N-hydroxysuccinamide and 206 mg (1.0 mmol) of N,N'-dicyclohexylcarbodiimide are added. The combined solutions are then stirred at 50C for 20 hours before removing precipitate by centrifugation. From the supernatant 130 mg (0.34 mmol) of the compound shown in formula 9b are isolated as yellow oil by preparative TLC with methanol/chloroform (1:19, v/v).

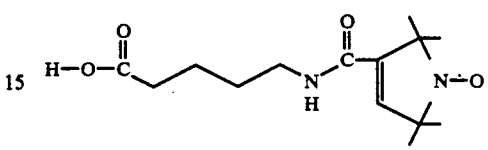

Formula 9a

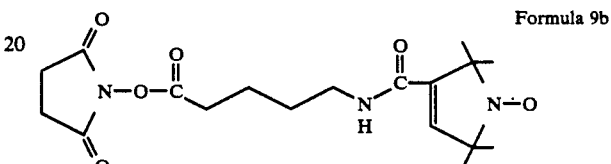

Formula 9b

These activated spin label compounds are then reacted with the modified nucleotides. This procedure is described by the following general example which teaches the reaction of any of the activated spin labeled compounds for example those shown in formulas 7, 8 or 9b with any of the activated nucleotides (formulas 4–6).

EXAMPLE 7

Condensation of the Activated Spin Labels with the Modified Nucleotides pppDUAA (4), pppDUPA (5) and pppDCAA (6)

Either of the above modified nucleoside triphosphates pppDUAA, pppDUPA, or pppDCAA can be condensed with any of the activated spin labels formulas 7, 8 or 9b to give the corresponding spin labeled nucleosides triphosphates.

0.03 mmol of the modified nucleoside triphosphate is dissolved in 2.5 ml of sodium borate buffer, pH 8.7. Addition of any one of the activated labels dissolved in 0.3 ml of N-N'-dimethyl formamide results in the formation of the spin labeled nucleosides triphosphate after 4 hours stirring at room temperature.

The products are purified by DEAE-Sephadex chromatography eluted with a 500 ml gradient of 0.1 to 0.5M ammonium bicarbonate. Additional purification can be achieved by preparative paper chromatography using Whatman 3MM paper eluted with ethanol/1.0M sodium acetate (7:3, v/v), or by HPLC with a micro-Bondapak C-18 column eluting with a step gradient (50 mM ammonium phosphate pH 7.5 (150 sec.) and 1:1 (v/v) ammonium phosphate pH 7.5/methanon-water (11:9, v/v) (999 seconds)).

Paper chromatography and/or HPLC purification is always followed by a final DEAE-Sephadex chromatography step to remove the non-volatile salts and by lyophilization. The typical yield of the coupling reaction is 40%–70% on a nucleoside basis. Specific neucloside triphosphates of the present invention include:

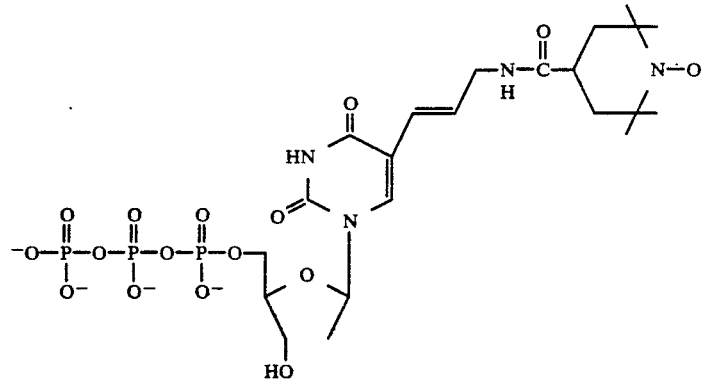
Formula 10
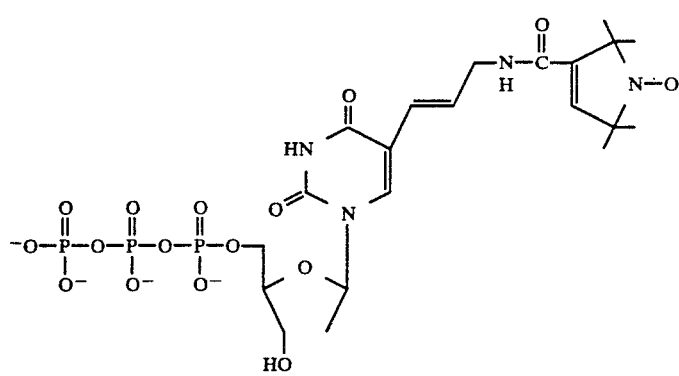
Formula 11
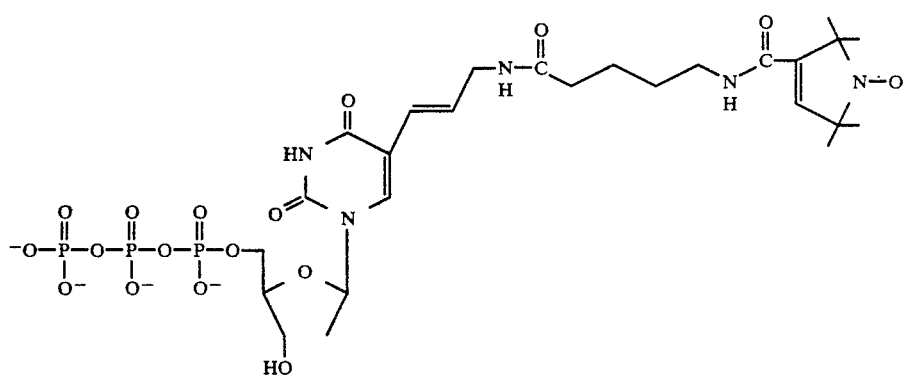
Formula 12
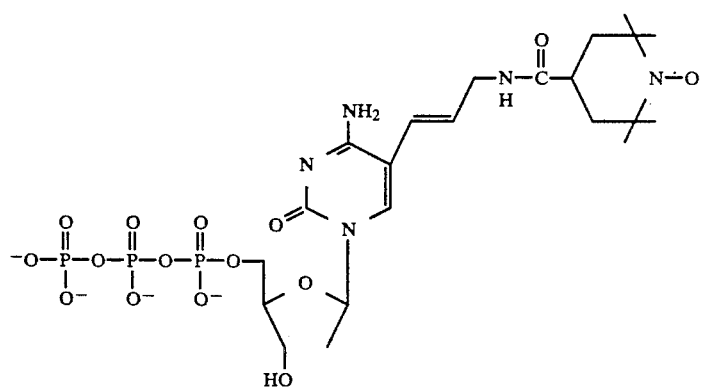
Formula 13

-continued
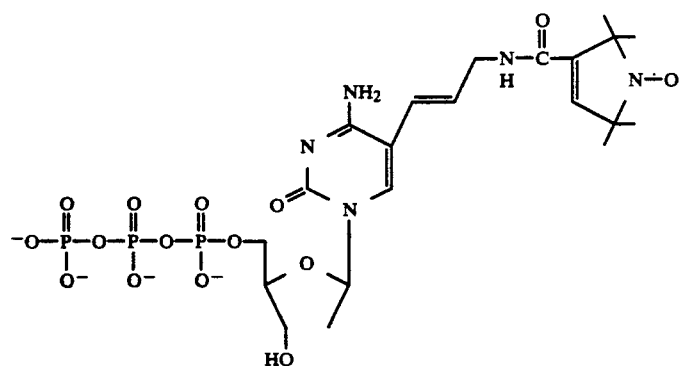
Formula 14
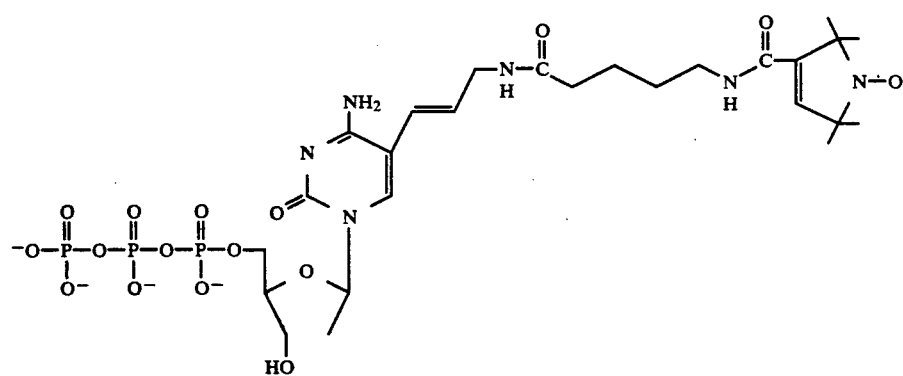
Formula 15
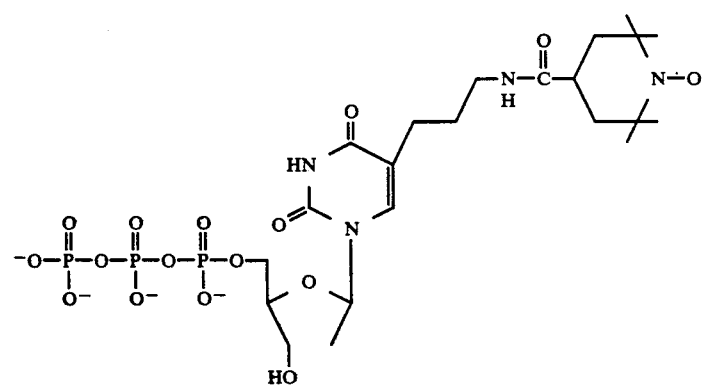
Formula 16
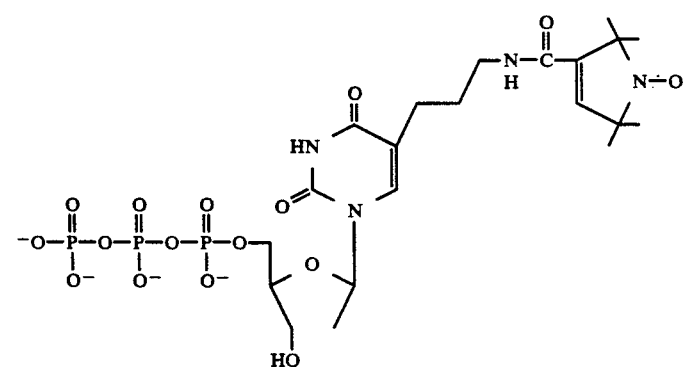
Formula 17

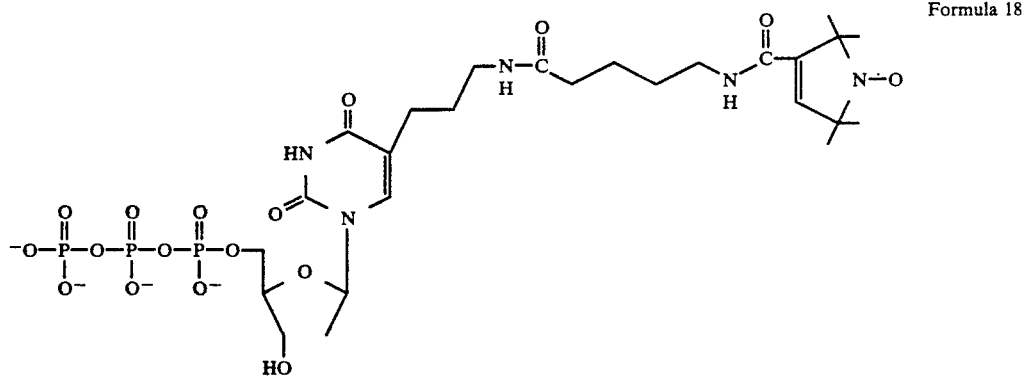

Formula 18

These nitroxide labeled compounds are then useful in the formulation of hybridization probes with template dependent enzymes such as in nick translation using *E. coli* Polymerase I or polymerization with T4 DNA polymerase according to standard techniques under conditions wherein all thymidylic acid building blocks or cytidylic acid building blocks are replaced with the corresponding nitroxide labeled building blocks. This forms a complimentary strand of a predetermined polynucleic acid. In other words, this produces DNA probes with nitroxide labeled residues of the nucleoside triphosphates of the present invention. This is further explained in the following general example. At least a portion of an unknown polynucleic acid sequence (RNA or DNA) can be detected by determining if the probe anneals to a single strand of the unknown polynucleic acid.

EXAMPLE 8

Nick Translation with pppDUAVAP (Formula 10) as Marker

All reactants are kept on ice and the water bath for the nick translation is set at 15C. 2 microgram of lambda DNA are nick translated in the presence of 2 nmol dCTP, 2 nmol dATP, dGTP, and 2 nmol pppDUAVAP (Formula 10) in 90 microliter of a buffer containing 50 mM Tris-HCl (pH 7.8), 5 mM $MgCl_2$, 10 mM 2-mercaptoethanol, and 10 microgram/ml nuclease free BSA after addition of 2 units of *E. coli* polymerase I and 200 picogram DNAase I. The reaction mixture is incubated for 90 minutes and then the reaction is stopped with 10 microliter of a 300 mM $Na_2$EDTA (pH 8.0) solution and 2.5 microliter of 5% (w/v) SDS.

The DNA incorporating the DUAVAP residue is separated from the unincorporated nucleotide triphosphates by Gel filtration on Sephadex G-25 or Sephadex G-50 with 0.15M sodium chloride and 0.015M sodium citrate, pH 7.0 as elution buffer. The first eluted peak contains the DUAVAP-labeled DNA based on its characteristic ESR lineshape.

The hybridization probe is removed from the DNA with a restriction enzyme and isolated by standard techniques such as alkaline sucrose gradient centrifugation or gel electrophoresis.

Nick Translation with DUAT (Formula 11) as Marker:

The same protocol as for the incorporation of DUA-VAP is used. The only difference consists in nick translating in the presence of 2 or 4 nmol of pppDUAT (Formula 11) instead of pppDUAVAP.

Incorporation of pppDUAVAP by T4 DNA Polymerase:

All reactants are kept on ice and the water bath for the enzymatic reactions is set at 37° C. 5.5 microgram of Hind III digestion of lambda DNA dissolved in 10.3 microliter 0.3M Na-acetate (pH 6.1) is added to 10 microliter of buffer A (50 mM Tris-acetate (pH 7.9), 50 mM Na-acetate, 10 mM Mg-acetate, 0.5 mM dithiothreitol, and 100 mg/ml nuclease free BSA. This solution is incubated with 5 units of T4 DNA polymerase for 15 minutes at 37° C. to allow 3'-5' exonuclease digestion. Thereafter polymerization is started by adding 7 microliter of buffer A containing 3 nmol of dCTP, 3 nmol of dATP, 3 nmol of dGTP, and 2 microliter of $H_2O$ containing 4 nmol of pppDUAVAP. The polymerization is allowed to proceed for 35 min. before stopping it with 10 microliter 300 mM $Na_2$EDTA (pH 8.0) and 2.5 microliter 5% (w/v) SDS. The DUAVAP labeled DNA is separated from the unincorporated nucleotide triphosphates by gel filtration on Sephadex G-50 with 0.15 sodium chloride and 0.015M sodium citrate, pH 7.0 as elution buffer. The first eluted peak contains the DUAVAP-labeled DNA based on its characteristic ESR lineshape.

ESR Detection of DUAVAP or DUAT Labeled DNA:

The nitroxide labeled DNA is detected by electron spin resonance. Specifically, nanomole quantities of the nitroxide labeled DNA are readily detected with a Varian E-104 spectrometer interfaced with an Apple II plus microcomputer. The characteristic 3 line ESR spectrum of the nitroxide labeled nucleotide undergoes a significant change upon incorporation with respect to the ratio of low field ($h_{-1}$) to mid peak field ($h_o$), $h_{-1}/h_o$, or the ratio of the high field ($h_{+1}$) to mid peak field ($h_o$), $h_{+1}/h_o$. These ratios are a function of the nitroxide label used. For the DUAT system the $h_{-1}/h_0$ is: $0.32 \pm 0.07$ for double stranded DUAT-labeled DNA, $0.65 \pm 0.04$ for single stranded DUAT-labeled DNA, and $0.87 \pm 0.02$ for unincorporated pppDUAT. For the DUAVAP system the $h_{-1}/h_o$ is: $0.6 \pm 0.03$ for double stranded DUAVAP labeled DNA, $0.7 \pm 0.02$ for single stranded DUAVAP labeled DNA, and $0.9 \pm 0.02$ for unincorporated pppDUAVAP labeled nucleotides. The characteristic spectra for the DUAT containing system are shown in the figure; (A) unincorporated pppDUAT; (B) single stranded DUAT labeled DNA; C) double stranded DUAT labeled DNA.

As with all these compounds, the relevant spectra is contained over a very narrow magnetic field. This provides the advantage of permitting detection of very nominal amounts of the nitroxide labeled DNA using a time averaging method.

More specifically, at X band with a microwave frequency of 9.5 GHz the ESR signal is at 3,300 gauss, scanned +/−50 gauss. However, ESR signals of nitroxide labeled DNA can also be observed with other bands (L-band, V band, etc.), i.e., all microwave frequencies varying from 0.5 to 35 GHz with the appropriate magnetic field. The magnetic field can be calculated with the standard resonance condition equation using a value of 2.005±0.001 for the g factor of the nitroxide labeled DNA.

Because the nitroxide labeled DNA is detected over such a narrow field it is particularly suitable for detection using a dedicated ESR which scans only that narrow field and time averages for the 3 characteristic peaks as shown in the Figure for a DUAT labeled DNA. Such a dedicated machine is less expensive, more accurate and less time consuming than any other method of detection.

Alternately, the nitroxide labeled polynucleotides can be detected colorimetrically. Basically when two nmol of a lattice which contains 10% labeled nucleotides is blotted onto a 0.45 micron nitrocellulose membrane or other appropriate support and baked at 80° C. under vacuum, the DNA blot can be visualized by the oxidation of hydroquinone to a dark brown insoluable matrix on the film. For that purpose the nitrocellulose membrane is submerged into a saturated solution of hydroquinone in ultra pure water at pH 7.0 in a heavy duty side arm flask. The flask is then saturated with oxygen and sealed under 15 psi oxygen for 24 hours. The hydroquinone solution is oxidized under these conditions and forms a brownish stain indicating the presence of the nitroxide labeled nucleic acid. Controls with unlabeled nucleic acid reveals no brown dot formation, thus the presence of nitroxides bound to a nucleic acid lattice has a catalytic affect on the oxidation of the hydroquinone. Of course this is substantially less preferred than the electron spin resonance method of detection since it incorporates basically many of the disadvantages of prior art detection methods, colorimetric methods, i.e., requiring multiple steps and the like.

Thus, by practicing the present invention, one is able to inexpensively and quickly detect DNA having incorporated therein the nitroxide labeled nucleotides of the present invention. Further, there is no problem with waste disposal since the nitroxide labeled nucleosides are not radioactive and present no significant environmental hazard.

We claim:

1. A 5'-triphosphate nucleotide wherein the base is selected from the group consisting of uracil and cytosine, said base substituted at the C-5 position of the pyrimidine ring with a carbon atom, said carbon atom further substituted with a nitroxide containing moiety wherein said nitroxide containing moiety has the following formula:

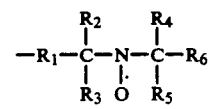

wherein $R_1$ represents $C_1$-$C_{15}$ alkylene;

$R_2$ and $R_4$ represent a moiety selected from the group consisting of $C_1$-$C_{15}$ alkyl and $C_2$-$C_{15}$ alkylene;

$R_3$, $R_5$, $R_6$ represents $C_1$-$C_5$ alkyl.

2. The nucleotide claimed in claim 1, having the following formula:

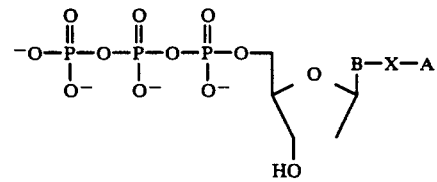

wherein the negative charges are balanced by biologically acceptable counterions.

wherein B represents uracil or cytosine;

X represents a group selected from the groups consisting of methenylene and methylene;

A represents said nitroxide containing moiety.

3. A nucleotide having the following

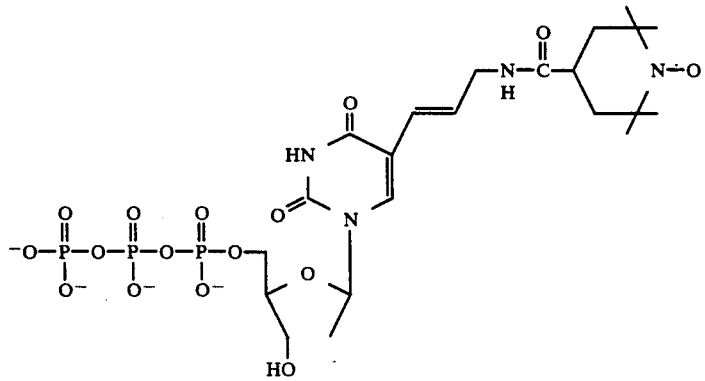

wherein the negative charges are balanced by biologically acceptable counterions.

4. A nucleotide having the following

However it is available should one want to detect these labels colorimetrically for example in a situation where one does not have the equipment required to record electron spin spectra.

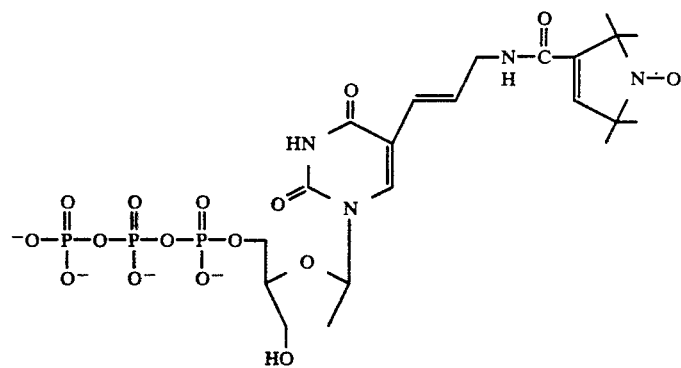

wherein the negative charges are balanced by biologically acceptable counterions.

5. A nucleotide having the following

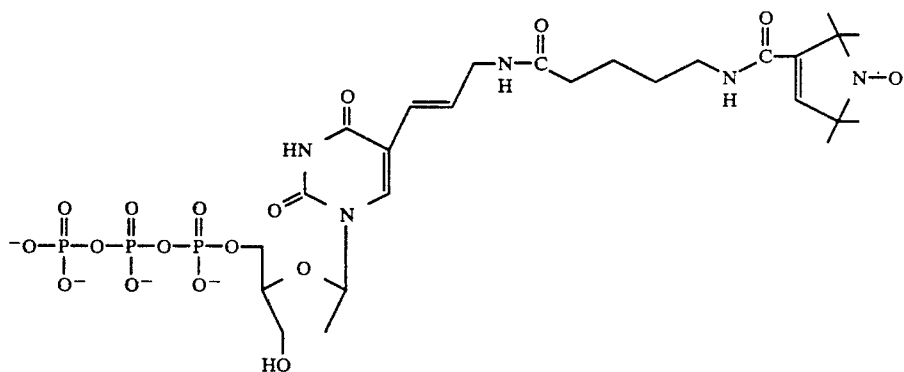

wherein the negative charges are balanced by biologically acceptable counterions.

6. A nucleotide having the following wherein the negative charges are balanced by biologically acceptable counterions.

7. A nucleotide having the following

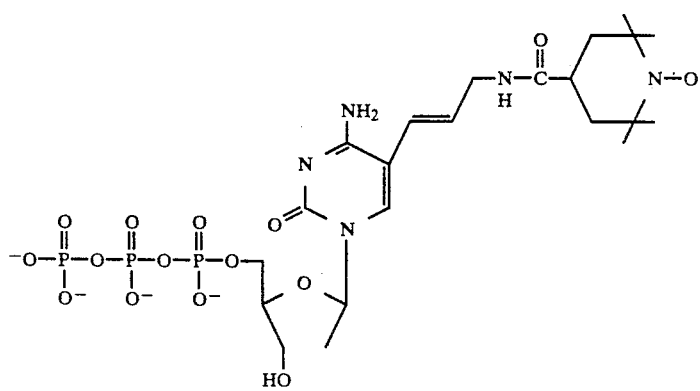

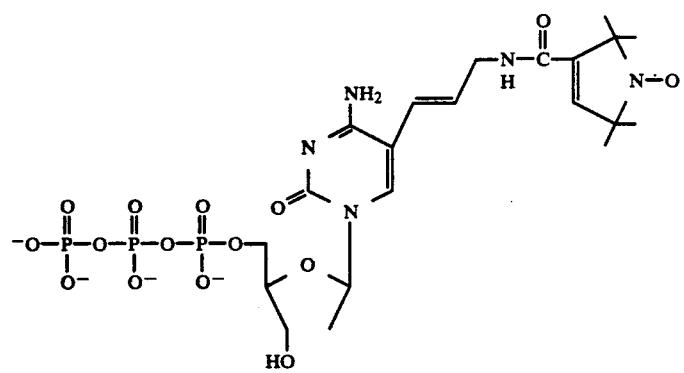

wherein the negative charges are balanced by biologically acceptable counterions.

8. A nucleotide having the following

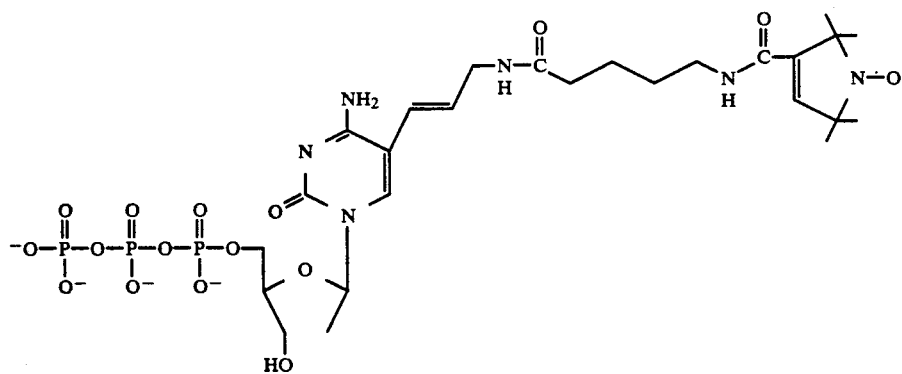

wherein the negative charges are balanced by biologically acceptable counterions.

9. A nucleotide having the following wherein the negative charges are balanced by biologically acceptable counterions.

10. A nucleotide having the following

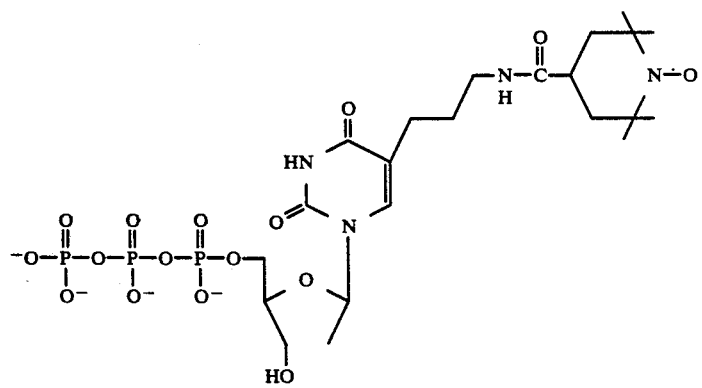

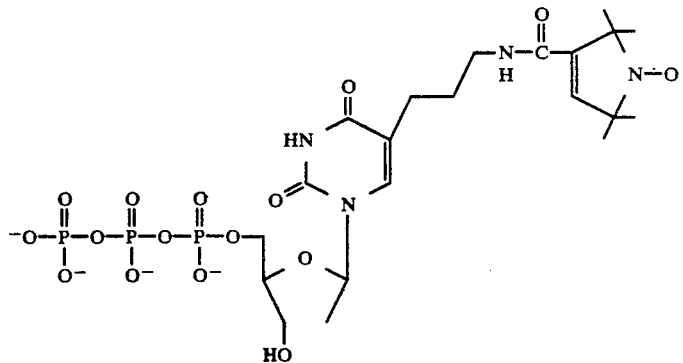
wherein the negative charges are balanced by biologically acceptable counterions.
11. A nucleotide having the following
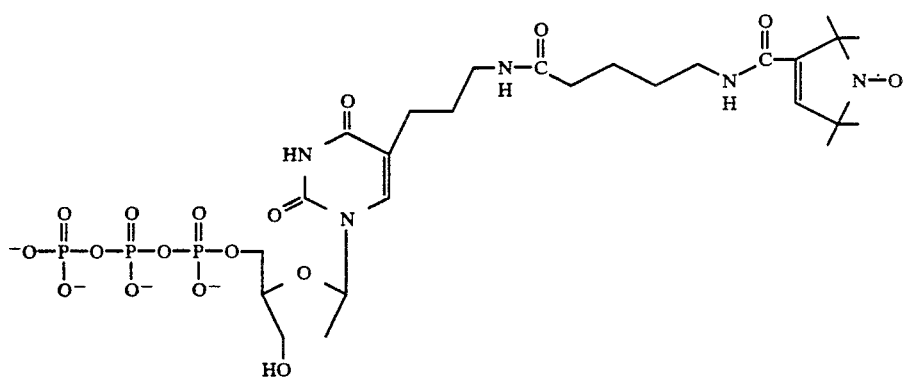
wherein the negative charges are balanced by biologically acceptable counterions.
* * * * *

UNITED STATES PATENT AND TRADEMARK OFFICE
CERTIFICATE OF CORRECTION

PATENT NO. : 5,004,809
DATED : April 2, 1991
INVENTOR(S) : Bobst et al.

It is certified that error appears in the above-indentified patent and that said Letters Patent is hereby corrected as shown below:

On the title page, column 1, insert immediately after the title, -- Research leading to the present invention was funded in part by the National Institute of Health, Grant No. AM-25252. Accordingly, the United States Government has certain rights in the invention. --

Signed and Sealed this

Twenty-ninth Day of November, 1994

Attest:

BRUCE LEHMAN

Attesting Officer    Commissioner of Patents and Trademarks